United States Patent [19]

Stahly

[11] Patent Number: 4,871,877

[45] Date of Patent: Oct. 3, 1989

[54] GEM-DISUBSTITUTED CYCLOHEXADIENONES AND THEIR PRODUCTION

[75] Inventor: G. Patrick Stahly, Baton Rouge, La.

[73] Assignee: Ethyl Corporation, Richmond, Va.

[21] Appl. No.: 196,680

[22] Filed: May 20, 1988

[51] Int. Cl.[4] ...................... C07C 49/675; C07C 45/71
[52] U.S. Cl. .................................... 568/326; 568/328; 568/348; 568/316; 568/377
[58] Field of Search ............... 568/316, 326, 328, 348, 568/377

[56] References Cited

U.S. PATENT DOCUMENTS

| | | | |
|---|---|---|---|
| 4,250,117 | 2/1981 | Takahashi et al. | 568/377 |
| 4,375,548 | 3/1983 | Wang | 568/812 |
| 4,448,980 | 5/1984 | Sogah | 556/436 |
| 4,634,787 | 1/1987 | Wang | 556/412 |
| 4,636,787 | 1/1987 | Wang | 556/470 |

FOREIGN PATENT DOCUMENTS 60-181040  9/1985  Japan .................................. 568/745

OTHER PUBLICATIONS

Yamagaki et al, Chem. Abst., vol. 105, #190,436d (1986).
Fujita et al., J. Am. Chem. Soc., 1985, 107, 4085–4087.

*Primary Examiner*—James H. Reamer
*Attorney, Agent, or Firm*—John F. Sieberth

[57] ABSTRACT

Quinones may be perfluoroalkylated by means of perfluoroalkyltrihydrocarbyl silane using certain active alkali metal salt catalysts and a proton source. The reaction—which is conducted, preferably in a suitable liquid phase reaction medium, most preferably a dipolar aprotic solvent—results in the formation of gem-disubstituted cyclohexadienones in which the gem substitutes are a perfluoroalkyl group and a hydroxyl group. These gem-disubstituted compounds in turn can be readily converted to perfluoroalkyl substituted aromatics, thus circumventing the traditional need for photochlorination followed by halogen exchange using hydrogen fluoride as a means of preparing perfluoroalkyl aromatic compounds.

46 Claims, No Drawings

GEM-DISUBSTITUTED CYCLOHEXADIENONES AND THEIR PRODUCTION

TECHNICAL FIELD

This invention relates in general to perfluoroalkyl aromatic compounds. More particularly, this invention relates to a new class of perfluoroalkyl substituted compounds from which perfluoroalkyl aromatic compounds can be readily produced and to novel methods by which such perfluoroalkyl substituted compounds may be prepared.

BACKGROUND

Perfluoroalkyl aromatic compounds such as benzotrifluoride, 4-chlorobenzotrifluoride and 3-aminobenzotrifluoride are used in the production of a variety of products such as pharmaceuticals, crop protection chemicals, germicides, dyes, and the like. The classical method of forming trifluoromethyl aromatics involves the photochemical side-chain chlorination of a methyl aromatic compound to form a perchloromethyl substituted aromatic which in turn is reacted with hydrogen fluoride to effect an exchange of fluorine atoms for the chlorine atoms on the methyl group. Ortho- and para-trifluoromethylphenols and anilines are even more difficult to make. They have been synthesized by photochemical side-chain chlorination or bromination of the appropriate nitrotoluene to form the perhalomethyl nitrobenzene. This product is treated with hydrogen fluoride to form the perfluoromethyl nitrobenzene, which is then reduced to the perfluoromethyl aniline. Diazotization and hydrolysis of the latter forms the perfluoromethyl phenol.

In Example 6 of U.S. Pat. No. 4,634,787, Wang reports that reaction between quinone and trichloromethyltrimethylsilane in tetrahydrofuran using tetrabutylammonium fluoride as catalyst yielded 4-(trichloromethyl)-4-(trimethylsilyloxy)-2,5-cyclohexadien-1-one. While the patentee refers to compounds having a —CX$_3$ group in which each X is independently halo, according to the patentee:

" ... preferably, each X is independently chloro or bromo. More preferably, each X is the same and is chloro or bromo. Even more preferably, each X is chloro. Preferred silanes [used as reactants in the process] are trichloromethylsilanes and the most preferred silane is trichloromethyltrimethylsilane."

THE INVENTION

In accordance with this invention there is provided a new class of perfluoroalkyl substituted compounds from which a wide variety of perfluoroaromatic compounds can readily be prepared. In addition, this invention provides a novel catalytic process by which these new perfluoroalkyl substituted compounds can be prepared.

The new perfluoroalkyl substituted compounds of this invention are gem-disubstituted cyclohexadienones in which the gem substituents are a perfluoroalkyl group and a hydroxyl group. These compounds are readily produced by reacting a quinone with a perfluoroalkyltrihydrocarbylsilane in the presence of an active catalyst and a proton source. These gem-disubstituted compounds in turn can be readily converted to perfluoroalkyl substituted aromatics. Thus this invention circumvents the traditional need for photochlorination followed by halogen exchange using hydrogen fluoride as a means of preparing perfluoroalkyl aromatic compounds.

The process of this invention preferably is conducted in a suitable liquid phase reaction medium. The preferred solvents or liquid reaction media for use in the process are dipolar aprotic solvents such as N,N-dimethylformamide, N,N-diethylformamide, N,N-dimethylacetamide, sulfolane, acetonitrile, hexamethylphosphoramide, nitrobenzene, dimethylsulfoxide, N-methylpyrrolidone, and the like. When performing the reaction in a substantially anhydrous aprotic solvent of low polarity such as tetrahydrofuran, 1,4-dioxane or the like, it is desirable to utilize a phase transfer catalyst such as a crown ether. See in this connection C. M. Starks and C. Liotta, *Phase Transfer Catalysts*, Academic Press, 1978.

Many different types of catalysts may be used in the process. These include alkali metal salts, trihydrocarbyl phosphites, hexahydrocarbyl phosphorous triamides, aminopyridines, quaternary ammonium bifluorides, and quaternary ammonium monofluorides.

One type of alkali metal salts that may be used are the active fluorine-containing salts, viz., potassium fluoride, rubidium fluoride, and cesium fluoride.

Another type of alkali metal salts that may be used are those which are devoid of fluorine with the proviso that they exhibit the appropriate catalytic activity. In this connection, not all such alkali metal salts exhibit a catalytic effect in the reaction and thus in any given instance where the suitability of a given fluorine-free alkali metal salt is not known, recourse should be had to the simple expedient of performing a few pilot experiments to determine whether the material will serve as a catalyst in the reaction. Alkali metal salts devoid of fluorine which are active catalysts in the process of this invention include the alkali metal azides such as lithium azide, sodium azide, and potassium azide; alkali metal cyanides such as sodium cyanide, potassium cyanide, and cesium cyanide; alkali metal hydroxides such as sodium hydroxide and potassium hydroxide; alkali metal carbonates such as potassium carbonate and cesium carbonate; and the like. Sodium carbonate, sodium nitrite, sodium phosphate are among materials deemed inactive as catalysts in the process of this invention.

Collectively, the trihydrocarbyl phosphites and the hexahydrocarbyl phosphorous triamides that may be used as catalysts in the process may be represented by the formula:

R$_3$P wherein all of the R groups are either hydrocarbyloxy groups or dihydrocarbylamino groups. Illustrative trihydrocarbylphosphites include trimethylphosphite, triethylphosphite, tripropylphosphite, triisopropylphosphite, tributylphosphite, tridodecylphosphite, triallylphosphite, trioleylphosphite, tricyclohexylphosphite, tricyclopropylcarbinylphosphite, triphenylphosphite, tritolylphosphite, tribenzylphosphite, phenyldiethylphosphite, dibenzyloctadecylphosphite, and the like. Among the hexahydrocarbylphosphorous triamides that may be employed as catalysts are hexamethylphosphorous triamide, hexaethylphosphorous triamide, hexapropylphosphorous triamide, hexaisopropylphosphorous triamide, hexabutylphosphorous triamide, hexacyclopentylphosphorous triamide, hexaphenylphosphorous triamide, hexa(4-ethylphenyl)phosphorous triamide, hexa(2-phenethyl)phosphorous triamide, hexacrotonylphosphorous triamide, and the like.

Various aminopyridine compounds may be used as catalysts in the process of this invention. These include such compounds as 2-aminopyridine, 3-aminopyridine, 4-aminopyridine and fused ring analogs thereof such as 4-aminoquinaldine, 2,3-diaminopyridine, 2,6-diaminopyridine, 3,4-diaminopyridine, and alkyl derivatives of any of the foregoing such as 2-dimethylaminopyridine, 4-dimethylaminopyridine, 4-diethylaminopyridine, and the like. Aminopyrazine and aminopyrimidines such as 2-aminopyrimidine and 4,5-diaminopyrimidine may also be used as catalyst in the process.

Another category of catalysts for the process are the bifluorides, notably quaternary ammonium bifluorides, quaternary phosphonium bifluorides, and alkali metal bifluorides. Collectively, these bifluoride catalysts may be represented by the formula:

$$Q^+HF_2^-$$

wherein Q is a quaternary ammonium group, a quaternary phosphonium group, or an alkali metal. Illustrative quaternary ammonium bifluorides include tetramethylammonium bifluoride, tetraethylammonium bifluoride, tetrabutylammonium bifluoride, cetyltrimethylammonium bifluoride, benzyltrimethylammonium bifluoride, and the like. Typical quaternary phosphonium bifluorides which may be employed include tetramethylphosphonium bifluoride, tetrathylphosphonium bifluoride, tetrabutylphosphonium bifluoride, decyltriethylphosphonium bifluoride, and the like. The alkali metal bifluorides are lithium bifluoride, sodium bifluoride potassium bifluoride, rubidium bifluoride and cesium bifluoride.

Still another group of catalysts that may be employed are the quaternary ammonium monofluorides. These are exemplified by such compounds as tetramethylammonium fluoride, tetraethylammonium fluoride, tetrabutylammonium fluoride, cetyl tripropylammonium fluoride, tricaprylmethylammonium fluoride, benzyltriethylammonium fluoride, benzyltrimethylammonium fluoride, benzyltributylammonium fluoride and the like.

Still other types of catalysts for the process may now occur to those skilled in the art from a perusal of this disclosure.

Carboxylic acids, water, alcohols, polyols, phenols, and the like exemplify the proton sources that may be used in the practice of this invention. The carboxylic acids may be cyclic (e.g., benzoic acid) or non-cyclic (e.g., acetic acid) and may be monocarboxylic acids (e.g., propionic acid) or polycarboxylic acids (e.g., succinic acid). Likewise, the alcohols may be cyclic (e.g., cyclohexanol) or non-cyclic (e.g., ethanol). The polyols may be linear (e.g., ethylene glycol) or branched (e.g., pentaerythritol). The phenols may be monohydric (e.g., phenol) or polyhydric (e.g., hydroquinone) and mononuclear (e.g., cresol) or polynuclear (e.g., 4,4'-dihydroxydiphenyl).

In selecting the catalyst proton source for use in a given reaction, care should be taken to use substances which do not adversely interact with the another. For example, one should not employ a carboxylic acid promoter with alkali metal salts such as the carbonates, cyanides, hydroxides, or etc.

The amount of catalyst used may be varied depending on the activity of the catalyst being used. Thus with some catalysts such as trihydrocarbylphosphites, hexahydrocarbylphosphorous triamides, aminopyridines, quaternary ammonium fluorides, quaternary ammonium bifluorides, and potassium carbonate, small catalytic quantities (e.g., as little as 0.10 mole per mole of quinone) may be used. With other catalysts such as KF, at least a stoichiometric amount relative to the quinone is desirable to achieve reasonable reaction rates (hours vs. days).

For best results, one should use a stoichiometric amount of the proton source relative to the quinone present in the reaction mixture. Desirably the amount of excess proton source, if used, should be kept as small as convenient, typically no more than about 5 to 10 percent above stoichiometric.

It is not known how or why the catalyst function in the process of this invention. Nor, is the structure or composition of the actual catalytic species known. All that is known is that when the catalyst is added to the reaction system in the form of an inorganic salt such as above-described, preferably in finely divided form, the reaction proceeds. When the catalyst is absent, no reaction occurs.

Of the catalyst-proton source systems described above, systems based on the above-referred to alkali metal salts, especially potassium or cesium fluorides, along with carboxylic acids, especially the lower fatty acids (acetic acid, propionic acid) are preferred.

In accordance with a particularly preferred embodiment of this invention, the reaction is performed in the presence of ammonium bifluoride which serves both as the catalyst and as the proton source. Thus with this substance it is unnecessary to use an acid, alcohol, water, or the like as a proton source.

Ordinarily the reaction will be conducted at temperatures within the range of about $-20°$ to about 100° C., although temperatures outside this range may be found useful in particular cases. Preferably, the temperature is maintained within the range of about 0° to about 25° C. throughout substantially the entire reaction period.

Quinones that may be used in the process of this invention include mononuclear and polynuclear quinones, both 1,2-quinones and 1,4-quinones. Election donating substituents, such as hydrocarbyl groups, groups, amino and mono- and dihydrocarbylamino groups, the hydroxyl group, and the like may be present in the quinones. A few exemplary quinones which may be used include 1,2-benzoquinone, 1,4-benzoquinone, 2-methyl-1,4-benzoquinone, 2-methoxy-1,4-benzoqinone, 2,5-dimethoxy-1,4-benzoquinone, 2-anilino-1,4-benzoquinone, 2,5-dianilino-1,4-benzoquinone, 2-phenyl-1,4-benzoquinone, polyporic acid, the ubiquinones, 2,3-dimethyl-1,4-benzoquinone, 2,5-dimethyl-1,4-benzoquinone, 1,4-naphthoquinone, 1-2-naphthoquinone, Vitamin K$_1$, Vitamin K$_2$, 2-methyl-1,4-naphthoquinone, anthraquinone, 2-methylanthraquinone, 2-ethylanthraquinone, 2-tert-butylanthraquinone, 1-aminoanthraquinone, 2-aminoanthraquinone, 1-amino-4-hydroxyanthraquinone, 1,2-diaminoanthraquinne, 1,4-diaminoanthraquinone, 1,5-diaminoanthraquinone, 2,6-diaminoanthraquinone, 1,8-diamino-4,5-dihydroxyanthraquinone, 1-hydroxy-4-(p-toluidino)anthraquinone, diphenoquinone, indanthrene blue, 1,2-dihydroxyanthraquinone, 9,10-phenanthraquinone, indanthrene violet, chrysophanic acid, and the like.

The perfluoroalkyltrihydrocarbyl silanes used in the process of this invention may be represented by the general formula R'SiR₃ where R' is a perfluoroalkyl group (trifluoromethyl, pentafluoroethyl, perfluorohexyl, etc.) and R, independently, is a hydrocarbyl group (alkyl, alkenyl, alkynyl, cycloalkyl, aryl, aralkyl, etc.). The number of carbon atoms in R and R' is irrelevant so long as the silane is co-reactive with the quinone in the process. A few illustrative compounds include trifluoromethyltrimethylsilane, tridecyltrifluoromethylsilane, trifluoromethyltrivinylsilane, triallyltrifluoromethylsilane, tricyclopentyltrifluoromethylsilane, tricyclopropylcarbinyltrifluoromethylsilane, trifluoromethyltriphenylsilane, trifluoromethyltri-(1-naphthyl)silane, tribenzyltrifluoromethylsilane, and corresponding and similar analogs containing the higher "homologous" perfluoroalkyl groups such as perfluoroethyl, perfluoropropyl, perfluoroisopropyl, perfluorobutyl, etc.

As noted above, this invention also provides gem-disubstituted cyclohexadienones in which the gem substituents are a perfluoroalkyl group and a hydroxyl group. In a preferred embodiment the perfluoroalkyl group is a trifluoromethyl group.

Among the preferred subclasses of compounds provided by this invention are the following:

4-hydroxy-4-trifluoromethyl-2,5-cyclohexadien-1-ones;
4-hydroxy-4-trifluoromethyl-2'-cyclohexadien-1-ones having an alkyl substituent in at least the 2 or 6 position;
1,4-dihydro-4-hydroxy-1-oxo-4-trifluoromethylnaphthalenes;
9,10-dihydro-10-hydroxy-9-oxo-10-trifluoromethylanthracenes;
2-hydroxy-2-trifluoromethyl-2,4-cyclohexadien-1-ones;
2-hydroxy-2-trifluoromethyl-2,4-cyclohexadien-1-ones having an alkyl substituent in at least the 4 or 6 position; and
9,10-dihydro-10-hydroxy-9-oxo-10-trifluoromethylphenanthrenes.

Illustrative gem-disubstituted compounds of this invention include:

4-hydroxy-4-trifluoromethyl-2,5-cyclohexadien-1-one;
4-hydroxy-4-pentafluoroethyl-2,5-cyclohexadien-1-one;
4-heptafluoropropyl-4-hydroxy-2-methyl-2,5-cyclohexadien-1-one;
2,5-dimethyl-4-hydroxy-4-trifluoromethyl-2,5-cyclohexadien-1-one;
4-hydroxy-4-nonafluorobutyl-2,5-cyclohexadien-1-one;
2-ethyl-4-hydroxy-4-trifluoromethyl-2,5-cyclohexadien-1-one;
2,4-dihydroxy-4-trifluoromethyl-2,5-cyclohexadien-1-one;
4-hydroxy-4-trifluoromethyl-2-methoxy-2,5-cyclohexadien-1-one;
4-hydroxy-4-trifluoromethyl-2,5-dimethoxy-2,5-cyclohexadien-1-one;
2-anilino-4-hydroxy-4-pentafluoroethyl-2,5-cyclohexadien-1-one;
2-hydroxy-2-trifluoromethyl-3,5-cyclohexadien-1-one;
6-ethyl-2-hdroxy-2-trifluoromethyl-3,5-cyclohexadien-1-one;
4,6-diethyl-2-hydroxy-2-trifluoromethyl-3,5-cyclohexadien-1-one;
1,4-dihydro-4-hydroxy-1-oxo-4-trifluoromethyl-4-naphthalene;
1,4-dihydro-4-hydroxy-2-methyl-1-oxo-4-trifluoromethylnaphthalene;
9,10-dihydro-10-hydroxy-9-oxo-10-pentafluoroethylanthracene;
1,4-diamino-9,10-dihydro-10-hydroxy-9-oxo-10-pentafluoroethylanthracene;
9,10-dihydro-1,2,10-trihydroxy-9-oxo-10-pentafluoroethylanthracene;
9,10-dihydro-10-hydroxy-9-oxo-10-pentafluoroethylphenanthrene; and
9,10-dihydro-1-ethoxy-10-hydroxy-9-oxo-10-pentafluoroethylphenanthrene.

The practice and advantages of this invention will become still further apparent from the following illustrative examples. Examples I and II illustrate the preparation of perfluoroalkyltrihydrocarbylsilanes, the class of reactants used in the process of this invention.

EXAMPLE I

Triethyltrifluoromethylsilane

A flask equipped with a dry ice condenser was flame dried under a nitrogen stream, and charged with 25 g (0.17 mol) of chlorotriethylsilane and 40 mL of dichloromethane. After cooling the resulting solution to $-78°$ C. and charging the condenser with dry ice and acetone, 40 mL (043 mol) of bromotrifluoromethane (Freon 13B1) that had been condensed into a graduated tube was warmed to room temperature and allowed to distill into the flask. The cold solution was treated dropwise with 66 mL (0.24 mol) of hexaethylphosphorous triamide, allowed to stir at $-78°$ C. for two hours, and allowed to stir at room temperature overnight. Low boiling components were then short path distilled into a cold ($-78°$ C.) receiving flask at $>1$ torr with the pot temperature kept at $<50°$ C. The distillate was further fractionated by removal of the dichloromethane ($40°$–$45°$ C. at atmospheric pressure) and short path distillation to give 22.0 g of 98% pure (69% yield) triethyltrifluoromethylsilane: bp $52°$–$54°$ C. at 10 torr; $^1$H NMR (CDCl₃) δ 0.59–1.16 (m); $^{19}$F NMR (CDCl₃, relative to CFCl₃) $-61.3$ ppm (s); IR (neat) 2960, 2915, 2882, 1458, 1413, 1206, 1055, 1020, 734, 693 cm$^{-1}$; mass spectrum (70 eV) m/z (relative intensity) 115 (66, M-CF₃), 105 (46), 87 (85), 77 (100), 59 (56), 49 (41), 47 (37), 41 (38). Anal. Calcd. for C₇H₁₅F₃Si: C, 45.62; H, 8.20. Found: C, 47.53; H, 8.56.

EXAMPLE II

Tri-n-butyltrifluoromethylsilane

A flask equipped with a dry ice condenser was flame dried under a nitrogen stream, and charged with 5.0 g (20 mmol) of chlorotri-n-butylsilane and 10 mL of dichloromethane. After cooling the resulting solution to $-78°$ C. and charging the condenser with dry ice and acetone, 6.2 mL (66 mmol) of bromotrifluoromethane (Freon 13B1) that had been condensed into a graduated tube was warmed to room temperature and allowed to distill into the flask. The cooling bath was removed and the mixture was allowed to warm to the temperature of the refluxing Freon ($-59°$ C.). To this cold solution was added, dropwise, 8.0 mL (29 mmol) of hexaethylphosphorous triamide. The resulting solution was stirred at reflux for 1 hour. Removal of the condenser and continued stirring for 1 hour resulted in evaporation of excess Freon and warming of the solution to room temperature. Dilution with 30 mL of dichloromethane, water (three 30 mL portions) and 1N HCl (two 30 mL portions) washing, drying (MgSO$_4$), and concentration afforded a residue which was short path distilled to give 3.6 g (64% yield) of tri-n-butyltrifluoromethylsilane: bp 53°–58° C. at 0.5 torr; $^1$H NMR (CDCl$_3$) δ 0.60–1.10 (m, 5H), 1.10–1.56 (m, 4H); $^{19}$F NMR (CDCl$_3$, relative to CFCl$_3$) −61.6 ppm (s); IR (neat) 2956, 2925, 2872, 1214, 1058 cm$^{-1}$; mass spectrum (70 eV) m/z (relative intensity) 199 (30, M-CF$_3$), 143 (80), 105 (30), 101 (27), 87 (30), 77 (66), 63 (43), 59 (41), 55 (54), 47 (25), 43 (20), 41 (100). Anal. Calcd. for C$_{13}$H$_{27}$F$_3$Si: C, 58.16; H, 10.14. Found: C, 58.26; H, 10.09.

Examples III through V illustrate the gem-disubstituted compounds of this invention and methods by which they may be prepared.

EXAMPLE III

4-Hydroxy-4-trifluoromethyl-2,5-cyclohexadien-1-one

A mixture of 74 mg (1.3 mmol) of ground ammonium bifluoride (NH$_4$HF$_2$), 119 mg (1.1 mmol) of 1,4-benzoquinone, and 2 mL of acetonitrile was treated with 239 mg (1.3 mmol) of triethyltrifluoromethylsilane and stirred vigorously at room temperature for 4 hours. The mixture was filtered and the filter cake was washed with dichloromethane. Concentration of the combined filtrates gave a black solid which was triturated with dichloromethane. The resulting mixture was filtered and the filter cake was washed with dichloromethane. Concentration of the combined filtrates afforded a brown solid which was purified by PTLC (one 2 mm silica gel plate eluted with a 2% methanol–98% dichloromethane) to give 83 mg (42% yield) of 4-hydroxy-4-trifluoromethyl-2,5-cyclohexadien-1-one.

EXAMPLE IV 4,6-Di-tert-butyl-2-hydroxy-2-trifluoromethyl-3,5-cyclohexadiene-1-one A mixture of 100 mg (1.7 mmol) of potassium fluoride, 132 mg (0.60 mmol) of 3,5-di-tert-butyl-1,2-benzoquinone, and 2 mL of acetonitrile was treated successively with 40 μL (0.70 mmol) of glacal acetic acid and 129 mg (0.70 mmol) of triethyltrifloromethylsilane, and stirred vigorously at room temperature for 15 minutes. The mixture was filtered and the filter cake was washed with dichloromethane. Concentration of the combined filtrates afforded a residue which was purified by PTLC (one 2 mm silica gel plate eluted with 20% dichloromethane—80% petroleum ether) to give 27 mg (16% yield) of 4,6-di-tert-butyl-2-hydroxy-2-trifluoromethyl-3,5-cyclohexadiene-one.

EXAMPLE V 1,4-Dihydro-4-hydroxy-1-oxo-4-trifluoromethylnaphthalene

A mixture of 74 mg (1.3 mmol) of ground ammonium bifluoride, 174 mg (1.1 mmol) of 1,4-naphthoquinone, and 1 mL of N,N-dimethylformamide was treated with 239 mg (1.3 mmol) of triethyltrifluoromethylsilane and stirred vigorously at room temperature for one hour. Gas chromatographic analysis of the reaction mixture showed that the major naphthalene-desired product was 1,4-dihydro-4-hydroxy-1-oxo-4-trifluoromethylnaphthalene.

Orthohydrocarbyl perfluoroalkyl phenolic compounds such as 2-alkyl- and 2,6-dialkyl-4-perfluoroalkylphenols, 2-alkyl-4-perfluoroalkylnaphthols and 6-alkyl- and 4,6-alkyl-2-perfluoroalkylphenols may be used as antioxidants and stabilizers in polymers, lubricants and like substrates normally susceptible to oxidative deterioration during storage or use, and as intermediates for the synthesis of phosphites, thiophosphites, phosphates, thiophosphates, and like products which may be used as antioxidants and as agricultural chemicals. Exemplary orthohydrocarbyl perfluoroalkyl phenolic compounds of this type include:

2-methyl-4-perfluoromethylphenol
2-ethyl-4-perfluoromethylphenol
2-isopropyl-4-perfluoromethylphenol
2-tert-butyl-4-perfluoromethylphenol
2-(2-octyl)-4-perfluoromethylphenol
2-benzyl-4-perfluoromethylphenol
2-cyclopentyl-4-perfluoromethylphenol
2,6-dimethyl-4-perfluoromethylphenol
2,6-diethyl-4-perfluoromethylphenol
2,6-isopropyl-4-perfluoromethylphenol
2,6-di-tert-butyl-4-perfluoromethylphenol
2-tert-butyl-6-methyl-4-perfluoromethylphenol
2-benzyl-6-methyl-4-perfluoromethylphenol
2-cyclopentyl-6-ethyl-4-perfluoromethylphenol
2-ethyl-4-perfluoroethylphenol
2-ethyl-4-perfluoropropylphenol
2-isopropyl-4-perfluoroethylphenol
2-tert-butyl-4-perfluoroethylphenol
2-(2-octyl)-4-perfluorobutylphenol
2,6-dimethyl-4-perfluoropentylphenol
2,6-diethyl-4-perfluoroethylphenol
2,6-isopropyl-4-perfluroisopropylphenol
2,6-di-tert-butyl-4-perfluoroethylphenol
2-tert-butyl-6-methyl-4-perfluorobutylphenol
2-methyl-4-perfluoromethylnaphthol
2-ethyl-4-perfluoromethylnaphthol
2-isopropyl-4-perfluoromethylnaphthol
2-tert-butyl-4-perfluoromethylnaphthol
2-(2-octyl)-4-perfluoromethylnaphthol
2-methyl-4-perfluoroethylnaphthol
2-ethyl-4-perfluoropropylnaphthol
2-isopropyl-4-perfluoroethylnaphthol
2-tert-butyl-4-perfluoroethylnaphthol
2-(2-octyl)-4-perfluorobutylnaphthol
2-benzyl-4-perfluoromethylnaphthol
2-cyclopentyl-4-perfluoromethylnaphthol
6-methyl-2-perfluoromethylphenol
6-ethyl-2-perfluoromethylphenol
6-isopropyl-2-perfluoromethylphenol
6-tert-butyl-2-perfluoromethylphenol
6-(2-decyl)-2-perfluoromethylphenol
6-benzyl-2-perfluoromethylphenol
6-cyclopentyl-2-perfluoromethylphenol
4,6-dimethyl-2-perfluoromethylphenol
4,6-diethyl-2-perfluoromethylphenol
4,6-isopropyl-2-perfluoromethylphenol
4,6-di-tert-butyl-2-perfluoromethylphenol
4-tert-butyl-6-methyl-2-perfluoromethylphenol
4-benzyl-6-methyl-2-perfluoromethylphenol
4-cyclopentyl-6-ethyl-2-perfluoromethylphenol
4-ethyl-2-perfluoroethylphenol
4-ethyl-2-perfluoropropylphenol
4-isopropyl-2-perfluoroethylphenol
4-tert-butyl-2-perfluoroethylphenol
4-(2-dodecyl)-2-perfluorobutylphenol 4,6-dimethyl-2-perfluoropentylphenol
4,6-diethyl-2-perfluoroethylphenol
4,6-isopropyl-2-perfluroisopropylphenol
4,6-di-tert-butyl-2-perfluoroethylphenol
4-tert-butyl-6-methyl-2-perfluorobutylphenol Orthohydrocarbyl perfluoroalkyl aromatic amines such as 2-alkyl- and 2,6-dialkyl-4-perfluoroalkyl anilines, 2-alkyl-4-perfluoroalkyl-1-naphthyl amines, and 6-alkyl- and 4,6-dialkyl-2-perfluoroalkyl anilines are useful as intermediates for the synthesis of crop protection chemicals such as herbicides and plant growth regulants and as intermediates for the synthesis of pesticides such as insecticides, miticides, acaricides, and fungicides.

Exemplary orthohydrocarbyl perfluoroalkyl aromatic amines include:

2-methyl-4-perfluoromethylaniline
2-ethyl-4-perfluoromethylaniline
2-isopropyl-4-perfluoromethylaniline
2-tert-butyl-4-perfluoromethylaniline
2-(2-octyl)-4-perfluoromethylaniline
2-benzyl-4-perfluoromethylaniline
2-cyclopentyl-4-perfluoromethylaniline
2,6-dimethyl-4-perfluoromethylaniline
2,6-diethyl-4-perfluoromethylaniline
2,6-isopropyl-4-perfluoromethylaniline
2,6-di-tert-butyl-4-perfluoromethylaniline
2-tert-butyl-6-methyl-4-perfluoromethylaniline
2-benzyl-6-methyl-4-perfluoromethylaniline
2-cyclopentyl-6-ethyl-4-perfluoromethylaniline
2-ethyl-4-perfluoroethylaniline
2-ethyl-4-perfluoropropylaniline
2-isopropyl-4-perfluoroethylaniline
2-tert-butyl-4-perfluoroethylaniline
2-(2-octyl)-4-perfluorobutylaniline
2,6-dimethyl-4-perfluoropentylaniline
2,6-diethyl-4-perfluoroethylaniline
2,6-isopropyl-4-perfluoroisopropylaniline
2,6-di-tert-butyl-4-perfluoroethylaniline
2-tert-butyl-6-methyl-4-perfluorobutylaniline
2-methyl-4-perfluoromethyl-1-naphthylamine
2-ethyl-4-perfluoromethyl-1-naphthylamine
2-isopropyl-4-perfluoromethyl-1-naphthylamine
2-tert-butyl-4-perfluoromethyl-1-naphthylamine
2-(2-octyl)-4-perfluoromethyl-1-naphthylamine
2-methyl-4-perfluoroethyl-1-naphthylamine
2-ethyl-4-perfluoropropyl-1-naphthylamine
2-isopropyl-4-perfluoroethyl-1-naphthylamine
2-tert-butyl-4-perfluoroethyl-1-naphthylamine
2-(2-octyl)-4-perfluorobutyl-1-naphthylamine
2-benzyl-4-perfluoromethyl-1-naphthylamine
2-cyclopentyl-4-perfluoromethyl-1-naphthylamine
6-methyl-2-perfluoromethylaniline
6-ethyl-2-perfluoromethylaniline
6-isopropyl-2-perfluoromethylaniline
6-tert-butyl-2-perfluoromethylaniline
6-(2-decyl)-2-perfluoromethylaniline
6-benzyl-2-perfluoromethylaniline
6-cyclopentyl-2-perfluoromethylaniline
4,6-dimethyl-2-perfluoromethylaniline
4,6-diethyl-2-perfluoromethylaniline
4,6-isopropyl-2-perfluoromethylaniline
4,6-di-tert-butyl-2-perfluoromethylaniline
4-tert-butyl-6-methyl-2-perfluoromethylaniline
4-benzyl-6-methyl-2-perfluoromethylaniline
4-cyclopentyl-6-ethyl-2-perfluoromethylaniline
4-ethyl-2-perfluoroethylaniline
4-ethyl-2-perfluoropropylaniline
4-isopropyl-2-perfluoroethylaniline
4-tert-butyl-2-perfluoroethylaniline
4-(2-dodecyl)-2-perfluorobutylaniline
4,6-dimethyl-2-perfluoropentylaniline
4,6-diethyl-2-perfluoroethylaniline
4,6-isopropyl-2-perfluoroisopropylaniline
4,6-di-tert-butyl-2-perfluoroethylaniline
4-tert-butyl-6-methyl-2-perfluorobutylaniline Still other products which may be produced from the gem-dicyclohexadienones of this invention include (i) novel gem-disubstituted cyclohexanols in which the gem-substituents are a perfluoroalkyl group and a hydroxy group, and (ii) novel gem-disubstituted cyclohexanones in which the gem-substituents are a perfluoroalkyl group and a hydroxyl group. Methods for effecting the synthesis of such compounds are illustrated in Examples VI through VIII below.

EXAMPLE VI

4-Trifluoromethylphenol

A solution of 200 mg (1.1 mmol) of 4-hydroxy-4-trifluoromethyl-2,5-cyclohexadien-1-one in 1 mL of absolute ethanol was treated successively with 147 mg (2.2 mmol) of zinc dust and 1 mL of a solution of 80% acetic acid—20% water. The mixture was heated to reflux for one hour, allowed to cool to room temperature, and poured into 20 mL of water. The resulting aqueous mixture was extracted with three 10 mL portions of diethyl ether. Combination, extraction with one 10 mL portion of 10% Na$_2$CO$_3$, drying (MgSO$_4$), and concentration of the ether layers afforded a residue which was subjected to PTLC (one 2 mm silica gel plate eluted with dichloromethane), giving 151 mg (83% yield) of 4-trifluoromethylphenol.

EXAMPLE VII 2,4-Di-tert-butyl-6-trifluoromethylphenol

A strip of aluminum foil weighing 293 mg (11 mmol) was amalgamated by immersion in a solution of 2% mercuric chloride in water for 15 sec., washed with absolute ethanol followed by diethyl ether, cut into small pieces, and added to a solution of 315 mg (1.1 mmol) of 4,6-di-tert-butyl-2-hydroxy-2-trifluoromethyl-3,5-cyclohexadien-1-one in 25 mL of 10% water—90% tetrahydrofuran. The resulting mixture was heated at 60°–70° C. for 2 hours, allowed to cool to room temperature, and filtered. The filter cake was washed with diethyl ether. Concentration of the combined filtrates gave a residue which was poured into 10 mL of water. The aqueous mixture was extracted with three 10 mL portions of dichloromethane. Combination, drying, and concentration of the organic layers gave a residue which was purified by PTLC (one 2 mm silica gel plate eluted with petroleum ether), affording 218 mg (73% yield) of 2,4-di-tert-butyl-6-trifluoromethylphenol.

EXAMPLE VIII

4-Trifluoromethylaniline

A mixture of 200 mg (11 mmol) of 4-hydroxy-4-trifluoromethyl-2,5-cyclohexadien-1-one, 461 mg (3.3 mmol) of ethyl glycinate hydrochloride, 336 mg (4.0 mmol) of sodium bicarbonate, and 3 mL of 95% ethanol was heated to reflux for 3 hours, allowed to cool to room temperature, and poured into 20 mL of water. The resulting aqueous mixture was extracted with three 10 mL portions of dichloromethane. Combination, drying (MgSO$_4$), and concentration of the organic layers afforded a residue which was subjected to PTLC (one 2 mm silica gel plate eluted with dichloromethane) to give 102 mg (56% yield) of 4-trifluoromethylaniline.

This invention is susceptible to considerable variation within the spirit and scope of the appended claims and thus is not intended to be limited by the exemplifications herein provided.

What is claimed is:

1. A process which comprises reacting under essentially anhydrous conditions a quinone with a perfluoroalkyltrihydrocarbylsilane in the presence of a catalyst and a proton source so that a gem-disubstituted cyclohexadienone is produced.
2. A process of claim 1 conducted in a liquid phase reaction medium.
3. A process of claim 1 wherein the quinone is a 4-quinone.
4. A process of claim 3 wherein the 1,4-quinone is a mononuclear 1,4-quinone.
5. A process of claim 3 wherein the 1,4-quinone is a polynuclear 1,4-quinone.
6. A process of claim 3 wherein the 1,4-quinone is a polynuclear fused ring 1,4-quinone.
7. A process of claim 1 wherein the quinone is a 1,2-quinone.
8. A process of claim 7 wherein the 1,2-quinone is a mononuclear 1,2-quinone.
9. A process of claim 7 wherein the 1,2-quinone is a polynuclear fused ring 1,2-quinone.
10. A process of claim 1 wherein the perfluoroalkyltrihydrocarbylsilane is a perfluoroalkyltrialkylsilane.
11. A process of claim 1 wherein the perfluoroalkyltrihydrocarbylsilane is a trifluoromethyltrihydrocarbylsilane.
12. A process of claim 1 wherein the perfluoroalkyltrihydrocarbysilane is a trifluoromethyltrialkylsilane.
13. A process of claim 1 wherein the catalyst is an alkali metal salt.
14. A process of claim 1 wherein the catalyst is a trihydrocarbylphosphite.
15. A process of claim 1 wherein the catalyst is hexahydrocarbylphosphorus triamide.
16. A process of claim 1 wherein the catalyst is an aminopyridine.
17. A process of claim 1 wherein the catalyst is a quaternary ammonium bifluoride.
18. A process of claim 1 wherein the catalyst is a quaternary phosphonium bifluroide.
19. A process of claim 1 wherein the catalyst is a quaternary ammonium monofluoride.
20. A process of claim 1 wherein the proton source is a carboxylic acid.
21. A process of claim 1 wherein the proton source is water.
22. A process of claim 1 wherein the proton source is a mono- or polyhydric alcohol or a mono- or polyhydric phenolic compound.
23. A process of claim 1 wherein the catalyst and the proton source is ammonium bifluoride.
24. A process of claim 1 wherein the reaction is performed in a liquid dipolar aprotic reaction medium.
25. A process of claim 1 wherein the reaction is performed in a liquid reaction medium comprising N,N-dimethylformamide, N,N-dimethylacetamide, sulfolane or acetonitrile.
26. A process of claim 1 wherein the reaction is performed in a liquid reaction medium consisting essentially of acetonitrile and wherein the catalyst is ammonium bifluoride.
27. A process of claim 1 wherein the temperature is maintained in the range of about 0° to about 25° C. throughout substantially the entire reaction.
28. A process which comprises reacting in a liquid phase reaction medium a 1,2- or 1,4-quinone with a trifluoromethyltrihydrocarbylsilane in the presence of an active catalyst and a proton source compatible with the catalyst so that a gem-disubstituted cyclohexadienone is produced.
29. A process of claim 28 wherein said catalyst is (a) an alkali metal salt, (b) a trihydrocarbylphosphite, (c) a hexahydrocarbylphosphorous triamide, (d) an aminopyridine, (e) a quaternary ammonium bifluoride, (f) a quaternary phosphonium bifluoride, or (g) a quaternary ammonium monofluoride.
30. A process of claim 28 wherein the proton source is a mono- or polyhydric alcohol or a mono- or polyhydric phenolic compound.
31. A process of claim 28 wherein the reaction medium comprises N,N-dimethylformamide, N,N-dimethylacetamide, sulfolane or acetonitrile.
32. A process of claim 28 wherein the temperature is maintained in the range of about 0° to about 25° C. throughout substantially the entire reaction.
33. A process of claim 28 wherein the trifluoromethyltrihydrocarbylsilane is a trifluoromethyltrialkylsilane; wherein said catalyst and said proton source is ammonium bifluoride; wherein the reaction medium consists essentially of N,N-dimethylformamide, N,N-dimethylacetamide, sulfolane or acetonitrile; and wherein the temperature is maintained in the range of about 0° to about 25° C. throughout substantially the entire reaction.
34. A gem-disubstituted cyclohexadienone in which the gem-substituents are a perfluoroalkyl group and a hydroxyl group.
35. A composition of claim 34 wherein the perfluoroalkyl group is a trifluoromethyl group.
36. A composition of claim 34 wherein said gem substituents are in the para-position relative to the keto group of the dienone.
37. A composition of claim 36, namely a 4-hydroxy-4-trifluoromethyl-2,5-cyclohexadien-1-one.
38. A composition of claim 34, namely a 4-hydroxy-4-trifluoromethyl-2,5-cyclohexadien-1-one having an alkyl substituent in at least the two or six position.
39. A composition of claim 34, namely 2,6-di-tert-butyl-4-hydroxy-4-trifluoromethyl-2,5-cyclohexadien-1-one.
40. A composition of claim 34, namely a 1,4-dihydro-4-hydroxy-4-trifluoromethylnaphthalene.
41. A composition of claim 34, namely a 9,10-dihydro-10-hydroxy-9-oxo-10-trifluoromethylanthracene.
42. A composition of claim 34 wherein said gem substituents are in the ortho-position relative to the keto group of the dienone.
43. A composition of claim 42, namely a 2-hydroxy-2-trifluoromethyl-2,4-cyclohexadien-1-one.
44. A composition of claim 42, namely a 2-hydroxy-2-trifluoromethyl-3,5-cyclohexadien-1-one having an alkyl substituent in at least the four or six position.
45. A composition of claim 42, namely 4,6-di-tert-butyl-2-hydroxy-2-trifluoromethyl-3,5-cyclohexadien-1-one.
46. A composition of claim 42, namely a 9,10-dihydro-10-hydroxy-9-oxo-10-trifluoromethylphenanthrene.

* * * * *